(12) United States Patent
Fischer et al.

(10) Patent No.: US 10,058,360 B2
(45) Date of Patent: Aug. 28, 2018

(54) SURGICAL INSTRUMENT FOR MANIPULATING, POSITIONING AND FIXING A SURGICAL ROD IN RELATION TO AN IMPLANT

(71) Applicant: Aesculap AG, Tuttlingen (DE)

(72) Inventors: Kay Fischer, Tuttlingen (DE); Sven Krüger, Trossingen (DE); Irene Marx, Trossingen (DE); Lisa Schneider, Alpirsbach (DE)

(73) Assignee: Aesculap AG, Tuttlingen (DE)

( * ) Notice: Subject to any disclaimer, the term of this patent is extended or adjusted under 35 U.S.C. 154(b) by 65 days.

(21) Appl. No.: 14/912,650

(22) PCT Filed: Aug. 20, 2014

(86) PCT No.: PCT/EP2014/067760
§ 371 (c)(1),
(2) Date: Feb. 18, 2016

(87) PCT Pub. No.: WO2015/024976
PCT Pub. Date: Feb. 26, 2015

(65) Prior Publication Data
US 2016/0199106 A1 Jul. 14, 2016

(30) Foreign Application Priority Data
Aug. 21, 2013 (DE) .................. 10 2013 109 058

(51) Int. Cl.
*A61B 17/70* (2006.01)
(52) U.S. Cl.
CPC ...... *A61B 17/7086* (2013.01); *A61B 17/7091* (2013.01)

(58) Field of Classification Search
CPC . A61B 17/70; A61B 17/7086; A61B 17/7091; A61B 17/88; A61B 17/8872
See application file for complete search history.

(56) References Cited

U.S. PATENT DOCUMENTS

| 5,810,878 A | 9/1998 | Burel et al. |
| 6,036,692 A | 3/2000 | Burel |

(Continued)

FOREIGN PATENT DOCUMENTS

JP    2001511678 A    8/2001

OTHER PUBLICATIONS

Notice of Allowance dated Jun. 11, 2012 for U.S. Appl. No. 12/397,807.
(Continued)

*Primary Examiner* — Julianna N Harvey
(74) *Attorney, Agent, or Firm* — RatnerPrestia

(57) ABSTRACT

A surgical instrument for manipulating and positioning a surgical rod relative to a surgical implant features two legs rotatably coupled to each other by a hinge. Each leg includes a working end. The working ends come into engagement with the implant upon closing the instrument by rotating the legs around the hinge and pivotally position the instrument relative to the implant around a swivel axis transverse to its longitudinal axis. At least one of the legs includes a contact structure for a surgical rod by which the rod is manipulated and positioned upon swiveling the instrument around the swivel axis relative to a rod seating of the implant. At least one of the legs includes a guide structure for guiding a fixation screw, to be screwed in, for the rod and/or for a tool for screwing in the fixation screw after having positioned the rod in the rod seating.

16 Claims, 9 Drawing Sheets

(56) References Cited

U.S. PATENT DOCUMENTS

Figure 1:
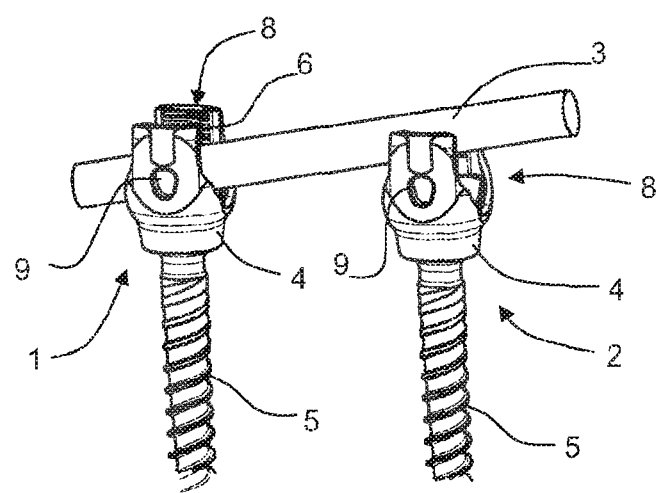

| | | |
|---|---|---|
| 8,449,549 B2 | 5/2013 | Barry |
| 2005/0149036 A1 | 7/2005 | Varieur |
| 2005/0261702 A1 | 11/2005 | Oribe |
| 2006/0095035 A1 | 5/2006 | Jones |
| 2007/0270868 A1 | 11/2007 | Dewey |
| 2007/0270869 A1 | 11/2007 | Young et al. |
| 2008/0234765 A1 | 9/2008 | Frasier |
| 2010/0185242 A1 | 7/2010 | Barry |
| 2010/0185248 A1 | 7/2010 | Barry |
| 2010/0228302 A1 | 9/2010 | Dauster |
| 2011/0184469 A1* | 7/2011 | Ballard .............. A61B 17/7091 606/279 |

OTHER PUBLICATIONS

Non Final Office Action dated Sep. 23, 2011 for U.S. Appl. No. 12/397,807.

International Search Report issued in related International Application No. PCT/EP2014067760, dated Nov. 4, 2014.

Written Opinion issued in related International Application No. PCT/EP2014/067760, dated Nov. 4, 2014.

German Search Report dated Feb. 28, 2014 for German Application No. 10 2013 109 058.3 with translation.

Notification of Reasons for Rejection for Japanese Application No. 2016-535473, dated Apr. 24, 2018, including English translation, 12 pages.

\* cited by examiner

SURGICAL INSTRUMENT FOR MANIPULATING, POSITIONING AND FIXING A SURGICAL ROD IN RELATION TO AN IMPLANT

RELATED APPLICATIONS

This application is the United States National Phase Entry under 35 U.S.C. § 371 of International Application No. PCT/EP2014/067760, filed Aug. 20, 2014, which is related to and claims the benefit of priority of German Application No. DE 10 2013 109 058.3, filed Aug. 21, 2013. The contents of International Application No. PCT/EP2014/067760 and German Application No. DE 10 2013 109 058.3 are incorporated by reference herein in their entireties.

FIELD

The present invention relates generally to surgical instruments, and in particular to a surgical instrument by means of which a surgical rod can be manipulated, positioned and fixed relative to an implant, in particular relative to a pedicle screw.

BACKGROUND

The use of pedicle screws is commonly known in surgery. As a rule, they are used in combination with a rod in order to fix vertebral bodies relative to one another, for example. In doing so, the pedicle screws are turned into vertebral bodies which are to be fixed relative to one another and subsequently are connected to one another usually with the aid of a rod. To this end, the head of the pedicle screw, which is also referred to as a tulip, has a recess which is U-shaped in most cases. For the mutual fixation of bones or bone pieces, the rod is inserted in the tulip and clamped in place therein with the aid of a screw fastening, so that the pedicle screws and hence the bones or bone pieces which have the screws driven into them are fixed relative to one another via the rod. The process of clamping the rod is usually carried out by use of grub screws, so-called set screws.

It may happen under certain circumstances that the rod prior to clamping it in place is not perfectly received in the tulip or only partially received therein. In such a case, it has to be correctly positioned in the tulip first; only then it can be clamped in the tulip in said position by screwing in the set screw. In order to position the rod in the recess of the pedicle screw, it is pressed into the tulip with an instrument which is referred to as a rod pusher or rod rocker or the pedicle screw is pulled up to it.

It is unavoidable that the rod which is pushed by force into the tulip with the aid of such an instrument is under mechanical tension in most cases. In this case, it is required to screw in the set screw into the tulip at least partially, while the rod is retained with the aid of the rod pusher, so that it remains in the dedicated recess of the tulip. The process of screwing in the set screw is usually performed with a screwdriver, while care has to be taken here that the pedicle screw does not turn during screwing in the set screw. Depending on the design of the implant, it is advantageous or even mandatory to introduce the set screw exactly in the direction of the thread axis, which may be problematic with certain operation conditions. Bearing this in mind, the prior art knows to provide a guiding arrangement in the implant for guiding the set screw and/or the screwdriver. It is also known to employ an auxiliary guiding instrument in addition to the rod pusher. In order to prevent the pedicle screw from turning upon driving in the set screw, it is known to use counter torque devices with which the pedicle screw is manually held by the surgeon or other surgical staff.

For positioning a surgical rod in an implant, the prior art knows various instruments. One example is a lever-type instrument, the one side of which comprises a handle and the opposite side of which comprises a fork-type instrument head. The instrument head can be pivotally arranged on the head of an implant, e.g. a pedicle screw, and comprises a lever-type spaced contact surface for the surgical rod. By swiveling the instrument around the head of the implant, the contact surface for the surgical rod is moved toward the rod seating of the pedicle screw. The rod can then be held in the desired position with the aid of the instrument. A disadvantage is that the arrangement and positioning of the instrument on the implant is afflicted with a certain instability, so that it may come loose in some circumstances. Furthermore, the instrument exclusively fulfils the function of positioning and holding the rod in the rod seating of the pedicle screw and to this end has to be manually held in the required position. It is disadvantageous that it does not offer any guidance which assists the surgeon during screwing in the set screw.

Another example for a known instrument is a pair of pliers whose implant-side pliers arms are formed into a seating for the head of a pedicle screw. The pair of pliers can be opened by the surgeon, can be arranged on the pedicle screw head so as to encompass it and can be closed subsequently, so that the seating of the pair of pliers is safely arranged on the screw head. The pair of pliers comprises a ratchet by means of which it remains in the closed position and it cannot be removed from the pedicle screw without releasing the ratchet. The plier arms have a lever-type design and comprise a contact surface for the surgical rod between them in the closed state, so that the latter can be inserted in a dedicated seating of the tulip by swiveling the pair of pliers around the pedicle screw head. It is easy to arrange the pair of pliers on the pedicle screw head, but a permanently reliable fit on the pedicle screw head requires a correct positioning and the application of a sufficient closing pressure. It is also necessary that the pair of pliers is manually held in the position which is required for positioning and clamping the surgical rod. It is disadvantageous that the instrument does not offer any guidance which assists the surgeon during screwing in the set screw.

Another known device comprises axially aligned, mutually concentric sleeves which can be moved relative to each other in axial direction by means of a lever ratchet mechanism. An inner sleeve is arranged on the head of a pedicle screw. An outer sleeve which is movable with respect to the inner sleeve comprises a seating for a surgical rod or forms such a seating. An actuation of the lever mechanism makes the outer sleeve together with the surgical rod move toward the inner sleeve which is arranged on the pedicle screw head, so that the rod is positioned relative to the screw head in the seating thereof. The inner spaces of the inner and outer sleeve simultaneously form a guide for a screw-driving tool for screwing in a set screw which is always aligned with the pedicle screw head.

Finally the patent document U.S. Pat. No. 8,449,549 B2 discloses in several embodiments an instrument realized as a sort of pliers which is termed as "Rod Coercer". It comprises two plier branches which are arranged on each other so as to be rotatable around a first hinge and comprise handles for a user-side actuation. The pedicle-screw side ends of the pair of pliers opposite to the handle side together form a contact surface for a surgical rod in the closed state of the pair of pliers. Each of the pedicle-screw side ends have an implant gripper arm arranged thereon so as to be able to swivel around a second hinge whose swivel axis is orthogonal to that of the first hinge. Upon opening the instrument, its implant gripper arms and its pedicle-screw side ends will open as well. During closing the instrument, its implant gripper arms and its pedicle-screw side ends will be closed, too. The instrument is applied on a pedicle screw in the opened state and is subsequently closed. In doing so, the implant gripper arms are supposed to enclose the pedicle screw head and the pedicle-screw side ends should rest against each other to a more or less defined extent and define the contact surface for the surgical rod. The pedicle-screw side ends are freely movable relative to each other in two directions in space due to the two swivel axes of the hinge being orthogonal to each other. As a consequence, the right working end may have another position than the left working end during use of the instrument, and the two working ends may get tilted relative to each other. Thus, the instrument does not provide the surgeon with a direct feeling and feedback with respect to the situation on the pedicle screw head. The handling of the instrument and in particular its positioning relative to the pedicle screw head and the surgical rod are difficult. The instrument does not comprise any guiding means for the set screw or for a tool for screwing in the set screw. The function of the instrument as a counter-torque device, in order to prevent the pedicle screw from being turned during screwing in the set screw, disadvantageously depends on the correct positioning on the pedicle screw head and a sufficiently high closing pressure of the instrument.

SUMMARY

Starting from the previously described prior art, the invention is based on the object to allow a surgeon to carry out a manipulation, positioning and fixation of a surgical rod relative to an implant screwed in a bone or a bone piece, in particular a pedicle screw, in a reliable fashion and within short time. Here, in particular the process of screwing a fixation screw for the rod into the implant is to be facilitated. The instrument is supposed to be able to be manufactured by simple ways and means and at low costs and it should be easy to apply for the surgeon using it.

The object is achieved by a surgical instrument for manipulating and positioning a surgical rod relative to a surgical implant, in particular a pedicle screw, the instrument being realized as a sort of pliers comprising two legs which are rotatably coupled to each other by means of a hinge, each of the legs comprising a working end, said working ends being intended and arranged to come into engagement with the implant upon closing the instrument by rotating the legs around the hinge and to pivotally position the instrument relative to the implant around a swivel axis which is transverse to its longitudinal axis, with at least one of the legs comprising a contact structure for a surgical rod, by means of which the rod is manipulated and positioned relative to a rod seating of the implant upon swiveling the instrument around the swivel axis, and wherein at least one of the legs is provided with a guide structure for guiding a fixation screw, to be screwed in, for the rod and/or for guiding a tool for screwing in the fixation screw after having positioned the rod in the rod seating.

The present invention allows to realize the functions of manipulating and positioning the rod on the one hand together with a guidance of the fixation screw and/or of the tool for screwing in the fixation screw and on the other hand in combination with the use of a single instrument and to avoid the need for the operating doctor to apply and hold a separate guiding instrument as well as the need of a third hand or an assistant. This is why the handling of the instrument is significantly simplified with respect to the prior art. As a separate handling of a guiding instrument for the fixation screw and for the tool for driving in the fixation screw is not necessary, it is possible with advantage to save time during a surgical procedure. The instrument according to the invention can be operated advantageously with one hand only, so that the surgeon can use his free hand for other purposes, in particular for screwing in the fixation screw. The process of screwing in the fixation screw is significantly simplified and mistakes are avoided. This is of advantage in particular in case of unclear surgical conditions, if the surgeon has to position and fix the rod without having an adequate view.

Having pressed down the rod, the fixation screw can be screwed in the rod seating or tulip substantially in load-free manner and with lateral guidance. This prevents the fixation screw from being obliquely screwed in the thread (cross-threading) which would mean that the thread might be damaged in some circumstance.

According to one embodiment, at least one working end of the legs of the instrument may comprise a pin or similar structure which upon closing the instrument by rotating the legs around the hinge engages a dedicated recess in the implant and is retained therein so as to be rotatable relative to the implant around the axis of the pin. In this embodiment, advantageously the entire instrument can be swiveled around the axis of rotation defined by the pin. This is why the surgeon is given a clear feeling, whether the instrument is correctly arranged on the implant and whether the rod is correctly placed in a desired position in the implant. A reliable fit of the instrument on the implant is ensured as well. Due to arranging pins in recesses of the implant, the instrument can indeed be swiveled around the swivel axis defined by the pins and recesses transverse to the implant's axis, but not around the implant's axis. In this way, the instrument advantageously acts as a rotation prevention during screwing in the fixation screw. According to the prior art, a separate counter-torque device was required for this purpose, so that this embodiment of the invention achieves a further simplification for the surgeon. What is more, the fixation screw can also be tightened with a high torque without transferring it to the implant.

According to a further embodiment, the guide structure is realized in the form of a preferably planar guide surface which is oriented to be perpendicular to the swivel axis of the instrument and forms the guide for the fixation screw and/or for the tool for screwing in the fixation screw independently of the swiveling angle of the instrument relative to the implant.

In other words, the guide structure is realized such that it offers a guidance or lateral support for the fixation screw and/or the tool across the entire expectable swiveling zone of the instrument and that the guide structure follows the respective swiveling angle.

According to a further embodiment, the contact structure is formed on one of the legs and extends substantially across the entire area between the legs if the instrument is closed. This ensures a reliable contact of the rod even if the instrument is not completely closed.

According to one embodiment, a curved protrusion is integrally formed on the working end of each of the legs, with the inner surfaces of the two protrusions substantially forming a prolongation of the rod seating and a lateral guide for the fixation screw and/or for the tool for screwing in the fixation screw or for the guide structure formed separately thereto.

According to one embodiment, the inner surfaces of the protrusions are plane-parallel to the swiveling plane in the closed position of the instrument.

According to one embodiment, the arc length of the protrusion corresponds to the expectable swiveling angle of the instrument. This ensures that the fixation screw and/or the tool for screwing in the fixation screw are laterally guided during the entire swiveling movement.

According to a further embodiment, at least one of the legs comprises a guide unit which has a partially cylindrical or cylindrical guide surface for the fixation screw and/or for the tool for screwing in the fixation screw and guided on a circular arc around the swivel axis of the instrument relative to the implant. In this embodiment, a guidance of the fixation screw and of the screw-in tool in two directions in space perpendicular to the longitudinal axis of the implant is always ensured.

According to a further embodiment, the guide unit comprises a bolt which is guided in a curved groove or guide track formed in the leg. The bolt may have a round, oval or elongated cross-section. In the case of a bolt with a round cross-section, the bolt in the guiding groove and hence the entire guide unit can be freely rotated, facilitating a correct arrangement and contact of the guide unit on the implant in certain conditions such as, for instance, an oblique or tilted application of the instrument on the implant. With other cross-sectional shapes, this free rotatability is prevented and an alignment of the guide unit relative to the swivel axis of the instrument around the implant is always ensured.

In particular, the bolt in the groove may be pretensioned into an end position with the aid of a spring in particular as a return member. In this end position, the guide unit is advantageously arranged and aligned relative to the instrument in such a manner that said guide unit rests flat on the implant upon applying the instrument on the implant, with the guide surfaces of the guide unit being already aligned in a suitable orientation for guiding the fixation screw and the tool. When the instrument is detached from the implant, the return member moves the guiding means back to the initial position.

According to a further embodiment, the guide unit may comprise a cylindrical through-hole whose inner wall forms the guide surface for the fixation screw and/or for the tool for screwing in the fixation screw. In this embodiment, a guidance for the fixation screw or for the screw-in tool in two directions in space perpendicular to the longitudinal axis of the implant is always ensured. Any occasion that the tool slips off is unlikely to occur due to the closed design of the guide and can be reliably prevented. According to a further embodiment, the guide unit may have a two-part design and each of the legs may have a part of the guide unit arranged thereon. In this way, also the second working end may comprise a forced guidance, a return member and a guiding means for a support pin or a support secured against rotation.

BRIEF DESCRIPTION OF THE DRAWING FIGURES

Figure 2:
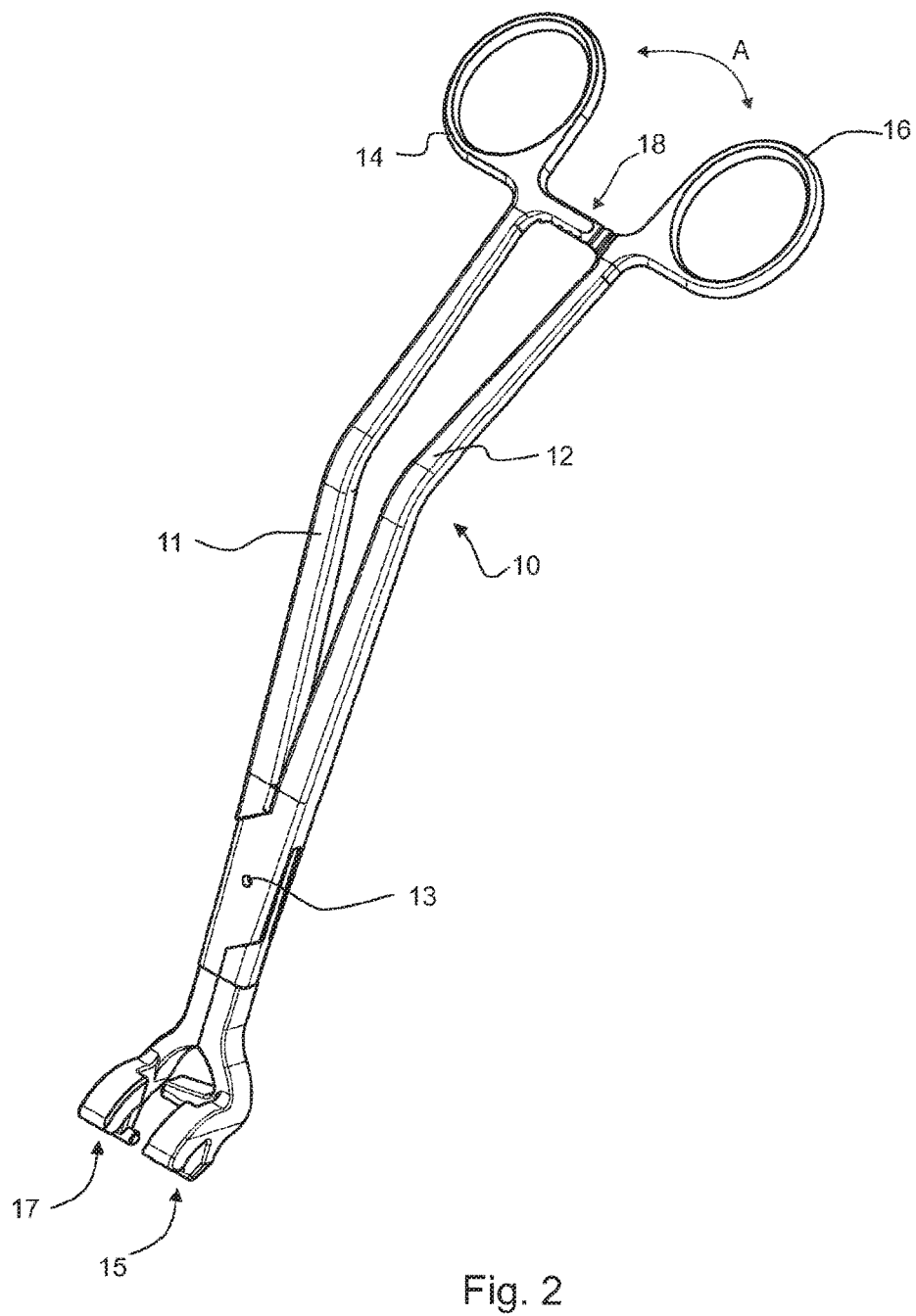
Figure 3:
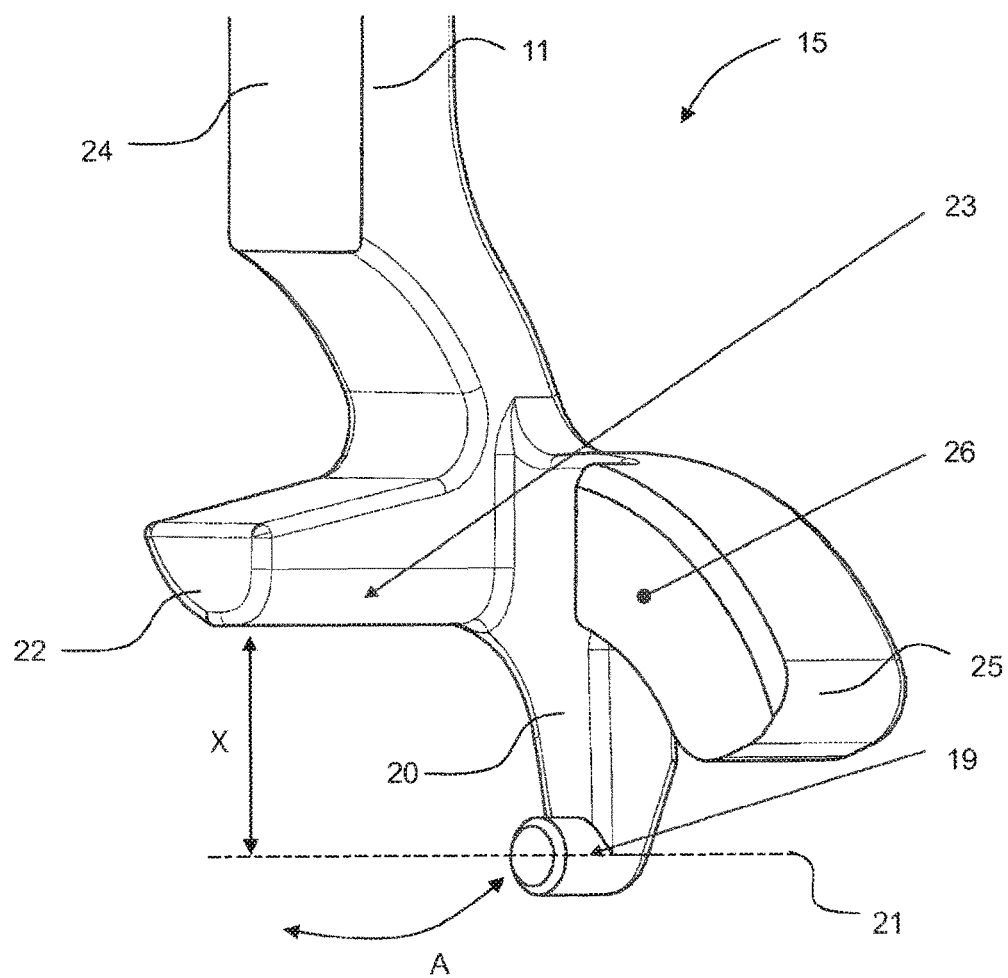
Figure 4:
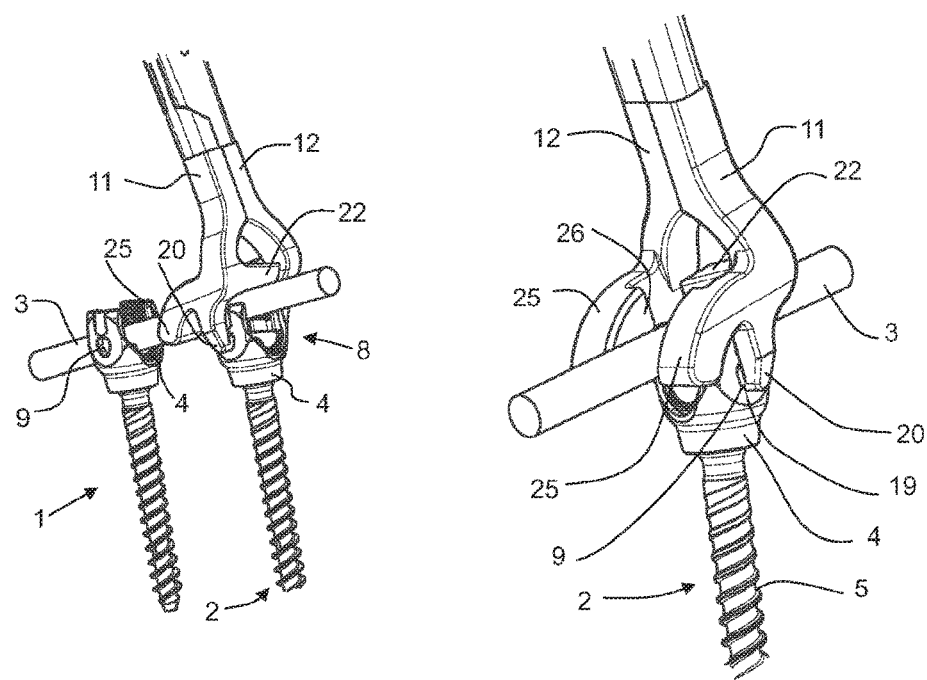
Figure 5:
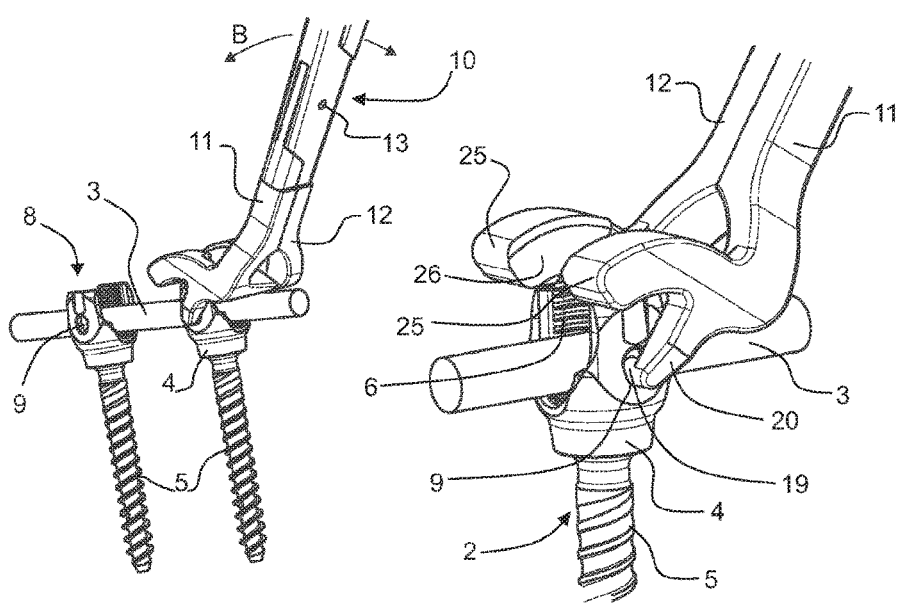
Figure 6:
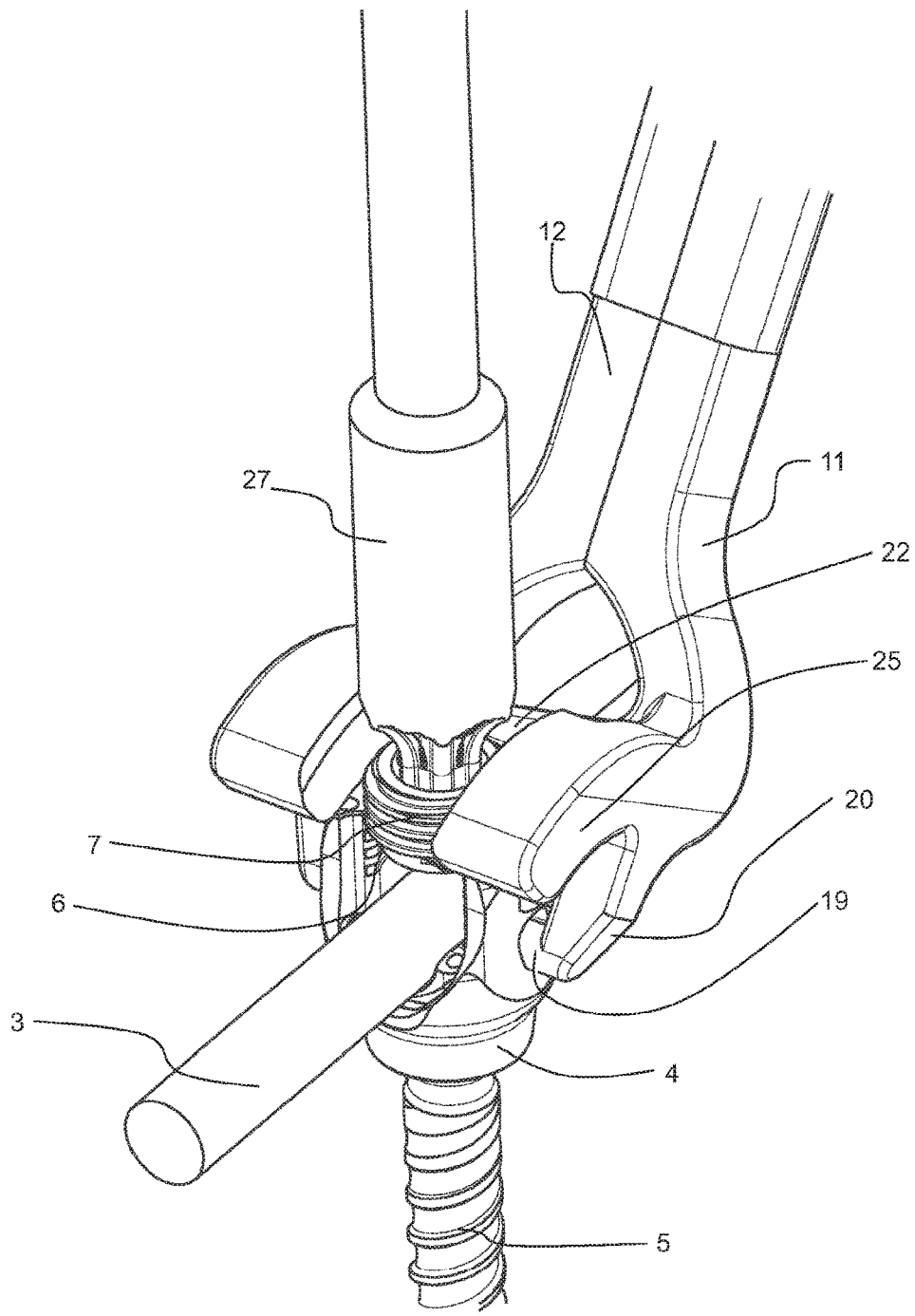
Figure 7:
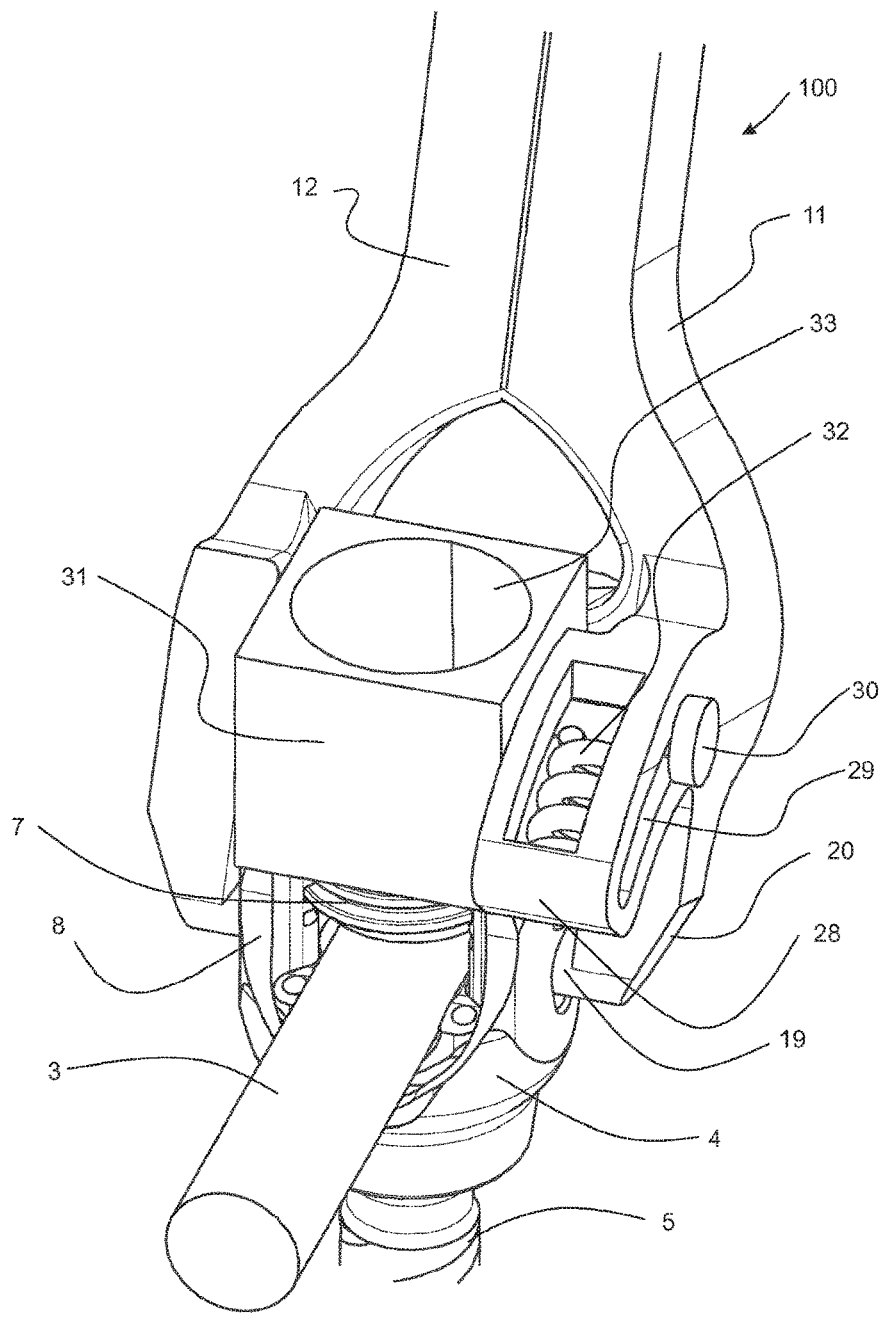
Figure 8:
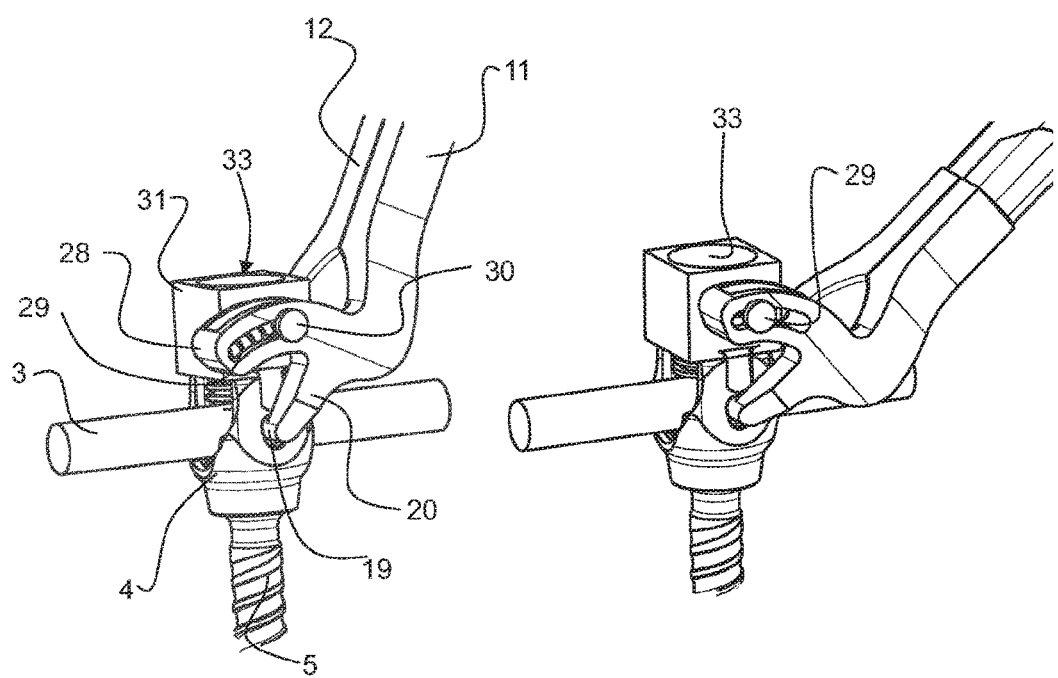
Figure 9:
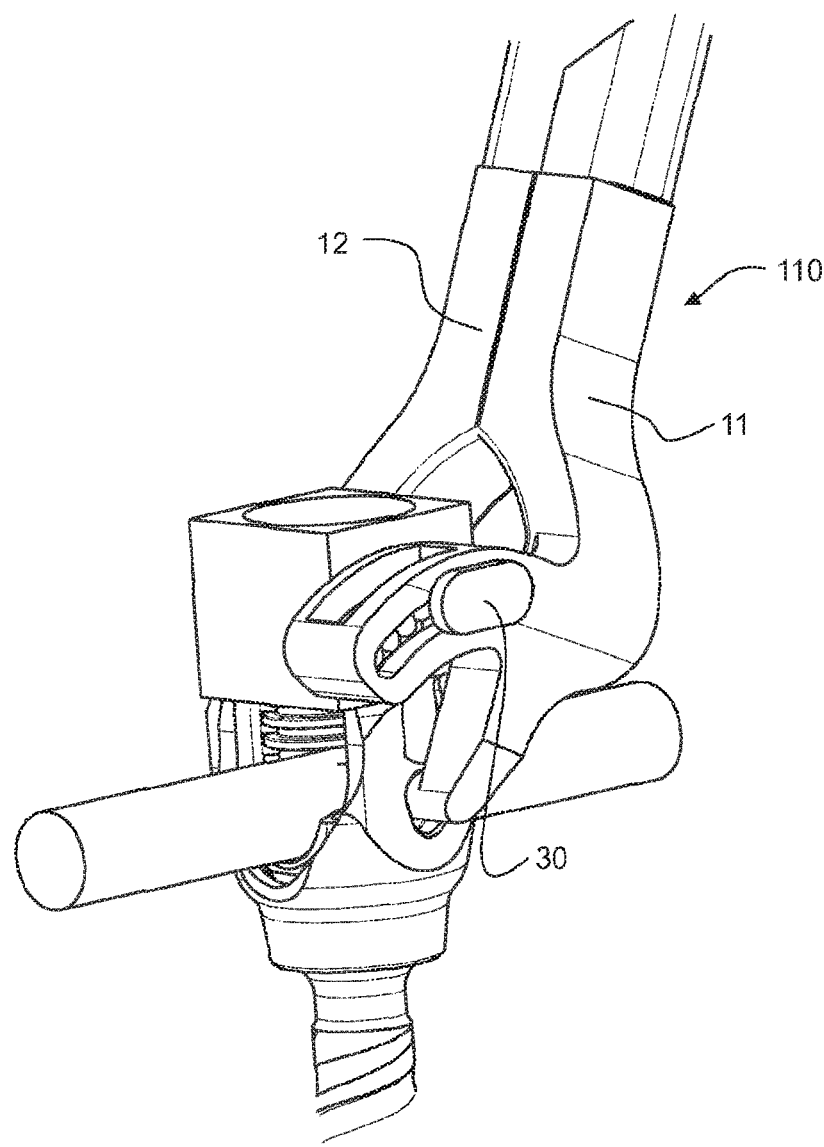

Further features and advantages of the present invention will be apparent from the following exemplary description of particularly preferred embodiments of the invention on the basis of the Figures in which:

FIG. 1 shows in a schematic perspective illustration a rod which is to be connected to two pedicle screws, FIG. 2 shows in a schematic perspective illustration a first embodiment of the instrument, FIG. 3 shows a working area of a leg of the instrument of FIG. 2 in an enlarged schematic perspective illustration, FIG. 4 shows the process of placing the instrument of FIGS. 2 and 3 on a pedicle screw as a first operational step, seen from two different viewing directions, FIG. 5 shows the process of pressing down the rod as a second operational step, seen form two different viewing directions, FIG. 6 shows the process of screwing in a fixation screw into the pedicle screw, FIG. 7 shows a second embodiment of the instrument in a schematic perspective illustration, FIG. 8 shows the use of the embodiment of FIG. 7 in two schematic views, and FIG. 9 shows a third embodiment of the instrument in a schematic perspective illustration.

DETAILED DESCRIPTION

FIG. 1 schematically shows a situation in the course of a spinal procedure in which two vertebrae (not shown in FIG. 1) are fixed relative to each other with the aid of two pedicle screws 1 and 2 as implants and by use of a surgical rod 3. Each of the pedicle screws 1, 2 comprises a head 4 which is also referred to as a tulip. The head 4 has a substantially U-shaped design and comprises a recess or rod seating 8 which is arranged and intended for clamping the rod 3. Adjoining the head 4, the pedicle screw 1, 2 comprises a shaft 5 which is provided with a bone thread which is screwed into the vertebra. Formed in the rod seating 8 of the head 4 is an internal thread 6 into which a fixation screw 7 (not shown in FIG. 1, but see FIG. 6 for instance) for the rod 3 is to be screwed in, the former also being referred to as a set screw. In the situation illustrated in FIG. 1, the rod 3 is placed in the rod seating 8 of the pedicle screw 1, but not fixed yet. At the outer side of the head 4 facing away from the rod seating 8, two opposite recesses 9 are formed of which only one can be seen in FIG. 1 in each case. Said recesses serve as support areas for bringing the instrument in contact with the pedicle screw, as will be explained in more detail below.

A first embodiment of the instrument 10 is shown in FIG. 2. The instrument 10 is realized as a sort of pliers comprising two legs 11, 12 and is shown in the closed state in FIG. 2. The two legs 11 and 12 are coupled to each other with the aid of a hinge 13 so as to be able to rotate around the axis thereof. One end of the leg 11 comprises a finger eyelet 14 and the opposite end comprises a shaped working end 15 which is shown in detail in FIG. 3. One end of the leg 12 comprises a finger eyelet 16 and the opposite end comprises a shaped working end 17. In the area of the finger eyelets 14, 16, the legs 11, 12 are latched or can be latched with each other by means of a ratchet mechanism 18. Upon releasing the ratchet mechanism 18, the legs 11, 12 can be spread apart while the two working ends 15,17 move away from each other.

The direction of movement of the working ends 15 during opening and closing the instrument 10 is marked in FIG. 3 with a double arrow A. The working end 15 comprises a pin 19 whose pin axis 21 extends substantially in the direction of movement, in other words is perpendicular to the axis of the hinge 13. The pin 19 is arranged on the end of one pin arm 20, projects toward the (not illustrated) working end 17 of the other leg 12 and is arranged and intended to engage in a recess 9 of the pedicle screw 1, 2, if the instrument 10 is placed thereon and closed.

A protrusion 22 acting as a contact structure for a surgical rod 3 is formed on the working end 15 so as to be spaced from the pin axis 21 by a lever arm X toward the opposite working end 17. The protrusion 22 comprises a curved contact surface 23 where the rod 3 rests and rolls or slides in case of a manipulation by means of the instrument 10. The protrusion 22 protrudes beyond the dividing plane of the instrument 10, along which the inner surface of the leg 11 extends which is designated in FIG. 3 with the reference numeral 24, and extends on the instrument 10 substantially across the entire area extending between the working ends 15, 17 in their closed condition. The pin axis 21 is substantially parallel to the contact surface 23.

Finally, the working end 15 comprises a protrusion 25 which is aligned to be tangential to the pin axis 21. The protrusion 25 has a curved design and is spaced from the pin axis 21 by its radius of curvature R. At the side of the protrusion 25 facing the opposite working end 17 of the leg 12, a planar guide surface 26 is formed. The latter is intended and arranged for guiding a set screw 7 and/or a tool 27 for driving in said screw.

The working end 17 the leg 12 is substantially mirror-inverted to the working end 15. However, the working end 17 does not have a protrusion 22 as contact structure for the surgical rod 3 (which can be seen clearly in FIG. 4). In the closed state of the instrument 10, the opposite guide surfaces 26 of the protrusions 25 form a sufficiently large gap, so that the rod 3 can be arranged between them with clearance. The distance between the guide surfaces 26 approximately corresponds to the diameter of a set screw or of a tool for driving it in, so that a guide is achieved in a direction in space (transverse to the hinge axis of the hinge 13).

The use and function of the embodiment illustrated in FIGS. 2 and 3 will now be described with reference to the FIGS. 4 to 6. In FIG. 4, the instrument 10 is shown from two different viewing directions after having applied it on the pedicle screw 2. In order to apply the instrument 10, it is grasped by an operator at the finger eyelet 14 and 16 and is opened, so that the working ends 15 and 17 and hence the pins 19 move away from each other. In the opened state, the instrument 10 can be arranged on the head 4 of the pedicle screw 2 and closed. During closing the instrument 10, the pins 19 of two working ends 15 and 17 enter the recesses 9 which are provided on the head 4 for this purpose. In combination with the pin 19 penetrating them, said recesses form a pivot bearing whose swivel axis extends transverse to the longitudinal axis of the pedicle screw 1, 2 and around which the entire instrument 10 can be swiveled relative to the pedicle screw 2 and the rod 3. The corresponding swing direction is illustrated in FIG. 5 with a double arrow B. During closing the instrument 10 (direction of movement A), the ratchet mechanism 18 comes into engagement, keeps the legs 11, 12 of the instrument 10 in the correspondingly closed position interconnected and locks it against any unintentional opening. In the state shown in FIG. 4, the instrument 10 is locked by the ratchet mechanism 18 and remains in said position if there is no intentional operation by the user. As is shown in particular in the left-hand diagram of FIG. 4, the rod 3 is positioned so as to be above the rod seating 8 and is not yet inserted therein.

In order to press the rod 3 into the rod seating 8, the instrument 10 still being in the closed state is swiveled by the surgeon around the swivel axis defined by the pin 19 and the recesses 9, in other words is swiveled around the pin axis 21. Said movement is schematically shown in FIG. 5 in two views from different viewing directions. In the course of the mentioned swiveling movement around the pin axis, the protrusion 22 has its curved contact surface 23 coming into engagement with the rod 3 and urges it further into the rod seating 8 with continued swiveling movement. With this swiveling movement, the opposite protrusions 25 move on a correspondingly curved path around the recesses 9 of the pedicle screw, with the guide surfaces 26 independently of the respective swiveling angle always remaining shortly above the head 4 comprising the rod seating 8. This ensures a guidance of the set screw and of the screw-in tool for the former independently of the swiveling angle which depends on the depth by which the rod 3 is pushed into the rod seating 8.

FIG. 6 finally shows the process of screwing the set screw 7 with the aid of a tool 27 into the internal thread 6 of the head 4 of the pedicle screw 1, 2. It can be seen that the mutually opposite guide surfaces 26 first guide the set screw 7 and then the tool 27 laterally if the screwing process is continued. In the illustrated embodiment, the guidance is effected transverse to the rod 3. FIG. 6 readily shows that the instrument 10—apart from the described functions of manipulating and positioning the rod 3 relative to the pedicle screw 1, 2 and inserting the rod 3 in the rod seating 8—fulfils as a further function the action of a counter-torque device which ensures in the course of screwing in the set screw 7 into the internal thread 6 that the pedicle screw 1, 2 (screwed into the bone) does not turn and is not farther driven into or out of the bone unintentionally. A rotation of the pedicle screw 1, 2 around its longitudinal axis relative to the instrument 10 is prevented by the pin 19 engaging the recesses 9.

A second embodiment of the invention in the form of an instrument 100 is shown in a schematic perspective illustration in FIG. 7. With the following exceptions, the instrument 100 is substantially identical to the instrument 10 shown in FIGS. 2 to 6. A curved protrusion 28 whose curvature extends around the pin 19 is formed only at the working end 15 of the leg 11. The protrusion 28 also has a curved guide track 29 the curvature of which extends around the pin 19 as the center. A bolt 30 of a guide unit 31 is guided in the guide track 29. The radius of the curvature of the guide track 29 corresponds to the distance between the axis of rotation of the instrument 100 around the head 4 (i.e. the longitudinal axis of the pin 19) and the mounting of the guiding means 31 in the guide track 29 (i.e. the longitudinal axis of the bolt 30). The bolt 30 can be translatorily shifted in the guide track 29 on the circular arc around the pin 19. As the bolt 30 has a round cross-section, it can also rotate around its longitudinal axis. As a consequence, the guide unit 31 firmly connected to the bolt 30 or formed in one piece with it can be translatorily moved together with the bolt 30 relative to the protrusion 28 and to the working end 15 on a curved path corresponding to the shape of the guide track 29 and can be rotated around the longitudinal axis of the bolt 30. A spring 32 is arranged in the guide track 29 beside the bolt 30 and urges the bolt 30 into the end position on the end of the guide track 29 illustrated in FIG. 7.

The guide unit 31 comprises a through-hole 33 which penetrates the guide unit in the direction of the longitudinal axis of the pedicle screw 1, 2. The through-hole 33 serves as a guide for a (not illustrated) set screw 7 and for a (not illustrated) screw-driving tool 27. In contrast to the embodiment of FIGS. 2 to 6, the embodiment of FIGS. 7 and 8 establishes a guide in two planes, i.e. transverse to the rod 3 and in the direction of its longitudinal axis.

FIG. 8 shows the use of this embodiment by means of two different positions of the instrument 100. FIG. 7 and the right-hand diagram of FIG. 8 show the instrument 100 in its orientation for applying it on the head 4 of the pedicle screw 1, 2. In this position, the guide unit 31 is urged into the upper right end position in the guide track 29 due to the action of the spring 32. In this position, the lower side of the guide unit 31 facing the head 4 of the pedicle screw 1, 2 is aligned to be parallel to the upper side of the head 4 and lies flat thereon with a full-area contact. The pins 19 engage the lateral recesses 9 of the pedicle screw 1, 2.

After having applied the instrument 100, it is swiveled around the swivel axis defined by the pin 19 and the recesses 9. As the guide unit 31 lies flat on the upper side of the head 4, it cannot follow said swiveling movement and is displaced relative to the working end 15 in the guide track 29, whereas it stays in the same position relative to the head 4 of the pedicle screw. Due to the swiveling movement, the rod 3 is urged into the rod seating 8, as has already been explained in the context with the embodiment of FIGS. 2 to 6. The process of screwing in the set screw can now be carried out in defined manner by being guided by the through-hole 33 in two directions in space. In doing so, the set screw 7 can be inserted into the rod seating 8 in the through-hole prior to applying the instrument 100 or only after having pushed in the rod 3. In other respects, the second embodiment corresponds to the first embodiment.

A third embodiment of the invention in the form of an instrument 110 is shown in FIG. 9 in a schematic perspective illustration. The instrument 110 is substantially the same as the instrument 100 of the FIGS. 7 and 8, with the exception that the bolt 30 does not have a round, but an elongated cross-section, so that it indeed is able to translatorily move along the guide track 29, but cannot be turned around its longitudinal axis. As a rotation of the guide unit 31 in the guide track 29 is not possible, its correct positioning so as to lie flat on the upper side of the head 4 of the pedicle screw 1, 2 is always ensured.

In a further embodiment not illustrated in the Figures but substantially corresponding to the embodiments of the FIGS. 7 to 9, the guide unit 31 is divided halfway. The one half of the guide unit 31 is guided in the guide track 29 of the leg 11. The other legs 12 also comprise a protrusion 28 including a guide track 29 where the second half of the guide unit 31 is guided in identical fashion. As for the rest, the third and fourth embodiments correspond to the first embodiment.

The invention claimed is:

1. A surgical instrument for manipulating and positioning a surgical rod relative to a surgical implant, wherein
the instrument comprises two legs which are rotatably coupled to each other by means of a hinge,
each of the legs comprises a working end, said working ends being intended and arranged to come into engagement with the implant upon closing the instrument by rotating the legs around the hinge and to pivotally position the instrument relative to the implant around a swivel axis which is transverse to its longitudinal axis,
at least one of the legs comprises a contact structure for a surgical rod, by means of which the rod is manipulated and positioned relative to a rod seating of the implant upon swiveling the instrument around the swivel axis,
at least one of the legs is provided with a guide structure for guiding a fixation screw, to be screwed in, for the rod after having positioned the rod in the rod seating, and
said working ends comprise a first working end and a second working end, wherein at least one of the first working end and the second working end comprises:
a curved protrusion; and
a pin arm separate from the curved protrusion, the pin arm having a pin on an end of the pin arm, said pin projecting toward the other of the first working end and the second working end, wherein
the curved protrusion has a radius of curvature and extends in a circular path around an axis of the pin, and
the curved protrusion is spaced from the axis of the pin by its radius of curvature.

2. The surgical instrument according to claim 1, wherein upon closing the instrument by rotating the legs around the hinge, the pin engages a dedicated recess in the implant and is retained therein so as to be rotatable relative to the implant around the axis of the pin.

3. The surgical instrument according to claim 1, wherein the guide structure is realized in the form of a guide surface which is oriented to be perpendicular to the swivel axis of the instrument and forms the guide for the fixation screw independently of the swiveling angle of the instrument relative to the implant.

4. The surgical instrument according to claim 1, wherein the contact structure is formed on one of the legs and extends substantially across the entire area between the legs if the instrument is closed.

5. The surgical instrument according to claim 1, wherein the guide structure or at least a part thereof is swiveled upon swiveling the instrument, and is swiveled around the proximal end of the implant.

6. The surgical instrument according to claim 1, wherein the guide structure or at least a part thereof laterally encompasses the implant in axial prolongation of the rod seating across the entire expectable swiveling zone of the instrument.

7. The surgical instrument according to claim 1, wherein each leg is formed in one piece, and the guide structure or at least a part thereof is arranged on the working end of said leg.

8. The surgical instrument according to claim 1, wherein said curved protrusion is integrally formed on said at least one of the first working end and the second working end, an inner surface of the protrusion substantially forming a prolongation of the rod seating and a lateral guide for the fixation screw and for the guide structure formed separately thereto.

9. The surgical instrument according to claim 1, wherein the guide structure comprises a guide unit which is guided on at least one of the legs on a circular arc around the swivel axis and comprises a partially cylindrical or cylindrical guide surface for the fixation screw.

10. The surgical instrument according to claim 9, wherein the guide unit comprises a bolt which is guided in a curved groove formed in the leg.

11. The surgical instrument according to claim 10, wherein the bolt is prestressed in the groove into an end position with the aid of a spring.

12. The surgical instrument according to claim 9, wherein the guide unit is two-part and each of the legs has one part of the guide unit arranged thereon.

13. The surgical instrument according to claim 9, wherein the guide unit comprises a cylindrical through-hole whose inner wall forms the guide surface for the fixation screw.

14. A surgical instrument according to claim 1, wherein a curvature of the curved protrusion extends around the pin.

15. A surgical instrument for manipulating and positioning a surgical rod relative to a surgical implant, wherein
the instrument comprises two legs which are rotatably coupled to each other by means of a hinge,
each of the legs comprises a working end, said working ends being intended and arranged to come into engagement with the implant upon closing the instrument by rotating the legs around the hinge and to pivotally position the instrument relative to the implant around a swivel axis which is transverse to its longitudinal axis,
at least one of the legs comprises a contact structure for a surgical rod, by means of which the rod is manipulated and positioned relative to a rod seating of the implant upon swiveling the instrument around the swivel axis,
at least one of the legs is provided with a guide structure for laterally guiding a tool for screwing in a fixation screw, to be screwed in, for the rod after having positioned the rod in the rod seating, and
said working ends comprise a first working end and a second working end, wherein at least one of the first working end and the second working end comprises:
a curved protrusion; and
a pin arm separate from the curved protrusion, the pin arm having a pin on an end of the pin arm, said pin projecting toward the other of the first working end and the second working end, wherein
the curved protrusion has a radius of curvature and extends in a circular path around an axis of the pin, and
the curved protrusion is spaced from the axis of the pin by its radius of curvature.

16. A surgical instrument for manipulating and positioning a surgical rod relative to a surgical implant, wherein
the instrument comprises two legs which are rotatably coupled to each other by means of a hinge;
each of the legs comprises a working end, said working ends being intended and arranged to come into engagement with the implant upon closing the instrument by rotating the legs around the hinge and to pivotally position the instrument relative to the implant around a swivel axis which is transverse to its longitudinal axis; and
at least one of the legs comprises a contact structure for a surgical rod, by means of which the rod is manipulated and positioned relative to a rod seating of the implant upon swiveling the instrument around the swivel axis,
wherein
at least one of the legs is provided with a guide structure for guiding a fixation screw, to be screwed in, for the rod after having positioned the rod in the rod seating, wherein
the guide structure comprises a guide unit which is guided on at least one of the legs on a circular arc around the swivel axis and comprises a partially cylindrical or cylindrical guide surface for the fixation screw, and wherein
the guide unit comprises a bolt which is guided in a curved groove formed in the leg.

* * * * *